(12) United States Patent
Gittard et al.

(10) Patent No.: US 9,943,335 B2
(45) Date of Patent: Apr. 17, 2018

(54) IMPLANTED MAGNETS RETRIEVAL SYSTEM AND METHOD

(71) Applicant: Cook Medical Technologies LLC, Bloomington, IN (US)

(72) Inventors: Shaun Davis Gittard, Winston-Salem, NC (US); Kanishka Ratnayaka, Washington, DC (US)

(73) Assignee: Cook Medical Technologies LLC, Bloomington, IN (US)

(*) Notice: Subject to any disclaimer, the term of this patent is extended or adjusted under 35 U.S.C. 154(b) by 349 days.

(21) Appl. No.: 14/788,920

(22) Filed: Jul. 1, 2015

(65) Prior Publication Data

US 2016/0081691 A1 Mar. 24, 2016

Related U.S. Application Data

(60) Provisional application No. 62/053,949, filed on Sep. 23, 2014.

(51) Int. Cl.
*A61B 17/52* (2006.01)
*A61B 17/11* (2006.01)
*A61B 17/00* (2006.01)

(52) U.S. Cl.
CPC ........ *A61B 17/52* (2013.01); *A61B 2017/003* (2013.01); *A61B 2017/00358* (2013.01); *A61B 2017/00876* (2013.01); *A61B 2017/00986* (2013.01); *A61B 2017/1107* (2013.01); *A61B 2017/1139* (2013.01)

(58) Field of Classification Search
CPC ............ A61B 17/11; A61B 2017/1135; A61B 2017/1107; A61B 2017/00876; A61B 17/1114; A61B 2017/1117; A61B 2017/1103; A61B 17/66; A61B 17/52; A61B 2017/003; A61B 2017/00358; A61B 2017/00986; A61B 2017/1139;

(Continued)

(56) References Cited

U.S. PATENT DOCUMENTS

| 5,690,656 | A | * | 11/1997 | Cope | .................... | A61B 17/11 |
| | | | | | | 128/898 |
| 5,895,404 | A | * | 4/1999 | Ruiz | .................... | A61B 17/11 |
| | | | | | | 600/11 |

(Continued)

*Primary Examiner* — Ahn Dang
*Assistant Examiner* — Erin Colello
(74) *Attorney, Agent, or Firm* — Liell + McNeil

(57) ABSTRACT

A method of retrieving a pair of previously implanted magnets from a patient's body includes maneuvering a guide catheter, which includes a guide magnet affixed to its distal end, toward the implantation site of the implanted magnets. The guide magnet is magnetically coupled to one of the implanted magnets in an orientation in which a through hole of the guide magnet is in register with through holes of the first and second implant magnets. An elongate capture member is slid through the lumen of the guide catheter until one of a proximal segment and a distal segment extends through the through holes of the guide magnet and the implanted magnets. An abutment segment of the elongate capture member, which separates the proximal segment and the distal segment is maneuvered into contact with the magnets. Then, the abutment segment, the guide magnet and the implanted magnets are moved as a group away from the implantation site.

20 Claims, 4 Drawing Sheets

(58) Field of Classification Search
CPC ........... A61M 25/0127; A61M 25/0158; A61F 2002/09528; A61F 2210/009
See application file for complete search history.

(56) References Cited

U.S. PATENT DOCUMENTS

| | | | |
|---|---|---|---|
| 6,632,229 B1 | 10/2003 | Yamanouchi | |
| 6,652,540 B1 | 11/2003 | Cole et al. | |
| 7,282,057 B2* | 10/2007 | Surti | A61B 17/1114 604/264 |
| 7,967,808 B2 | 6/2011 | Fitzgerald et al. | |
| 8,262,680 B2 | 9/2012 | Swain et al. | |
| 8,437,833 B2 | 5/2013 | Silverstein | |
| 8,556,919 B2 | 10/2013 | Aguirre et al. | |
| 8,628,548 B2 | 1/2014 | Aguirre et al. | |
| 2005/0182429 A1* | 8/2005 | Yamanouchi | A61B 17/11 606/153 |
| 2008/0208224 A1* | 8/2008 | Surti | A61B 17/1114 606/153 |
| 2009/0125042 A1 | 5/2009 | Mouw | |
| 2010/0036399 A1* | 2/2010 | Viola | A61B 17/11 606/153 |
| 2011/0144560 A1* | 6/2011 | Gagner | A61B 17/1114 604/8 |

* cited by examiner

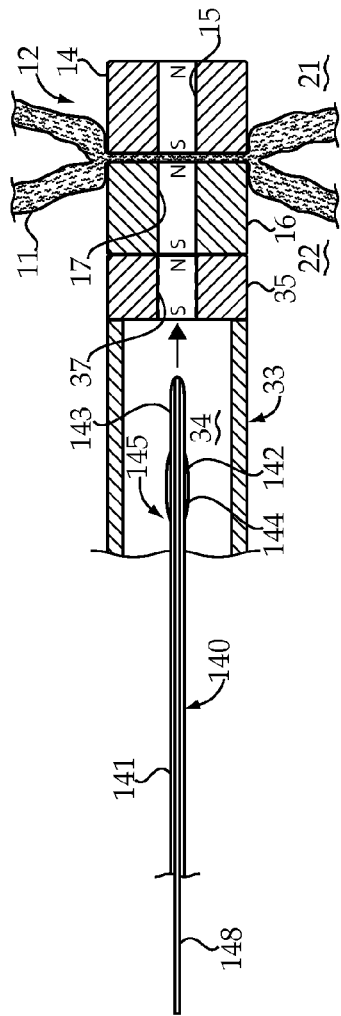
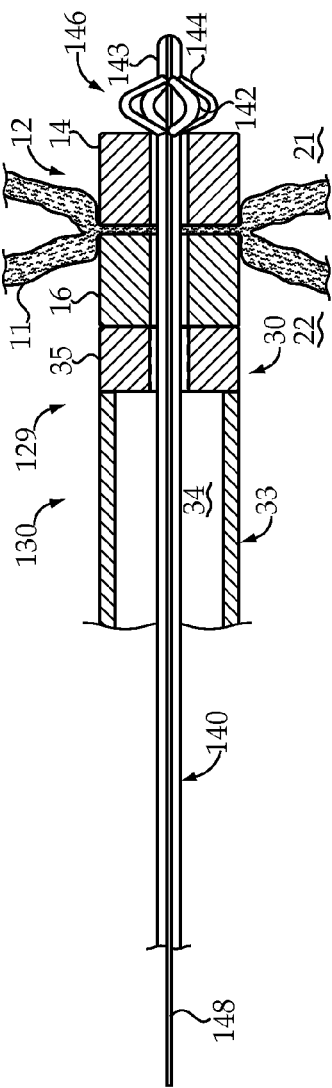
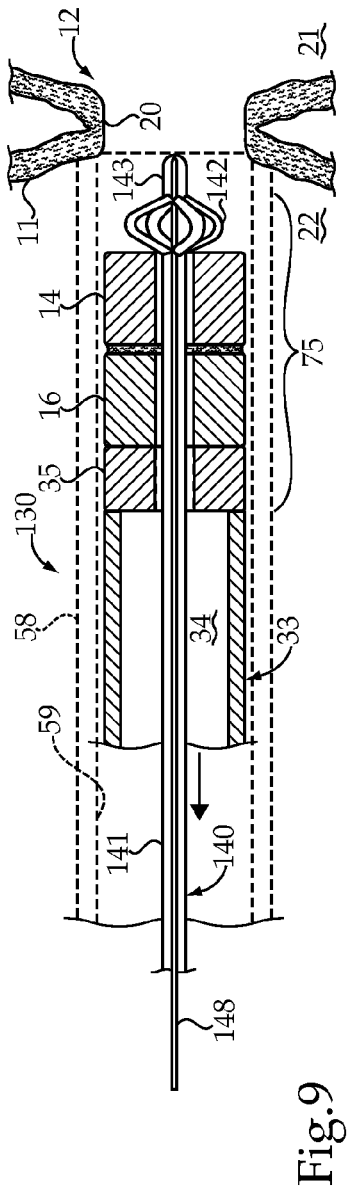
Fig.7
Fig.8
Fig.9

IMPLANTED MAGNETS RETRIEVAL SYSTEM AND METHOD

GOVERNMENT RIGHTS

This invention was created in the performance of a Cooperative Research and Development Agreement with the National Institutes of Health, and Agency of the Department of Health and Human Services. The Government of the United States has certain rights in this invention.

TECHNICAL FIELD

The present disclosure relates generally to a retrieval system for implanted magnets, and more particularly to a magnetic retrieval system for a pair of implanted magnets that define through holes in register with each other.

BACKGROUND

Magnetic compression and anastomosis is a strategy by which first and second magnets are located in respective volumes within a patient. The two magnets are magnetically linked to compress the walls defining the respective volumes together. For instance, co-owned U.S. Pat. No. 8,556,919 teaches a delivery system for magnet anastomosis in which the tissue compressed between a pair of implanted magnets causes a necrosis of the walls of the stomach and jejunum until an anastomosis is formed. This reference suggests that, after the anastomosis is formed, the implanted magnets can pass through the body naturally or can be removed by strategies such as laparotic removal, or possibly an endoscopic removal. While these strategies for removal of implanted magnets may be attractive and feasible for creating an anastomosis in the digestive system, these suggested retrieval strategies may not be realistically feasible in other body volumes, such as creating an anastomosis between two cardiovascular passageways in a patient.

The present disclosure is directed toward one or more of the problems set forth above.

SUMMARY

In one aspect, a magnet retrieval system includes a guide catheter that defines a lumen and includes a guide magnet affixed to a distal end, and the guide magnet defines a through hole in communication with the lumen. An elongate capture member is slidably received in the lumen and includes an abutment segment separating a proximal segment from a distal segment. A first implant magnet is magnetically coupled to a second implant magnet. A through hole defined by the first implant magnet is in register with a through hole defined by the second implant magnet. The magnet retrieval system has a retrieval configuration in which the guide magnet is magnetically coupled to one of the first implant magnet and the second implant magnet, and one of the proximal segment and the distal segment of the elongate capture member extends through the through holes of the guide magnet, the first implant magnet and the second implant magnet. Also, the abutment segment is in contact with one of the guide magnet, the first implant magnet and the second implant magnet.

A method of retrieving previously implanted magnets from an implantation site includes maneuvering a guide catheter toward the implantation site. The implanted magnets include a first implant magnet magnetically coupled to a second implant magnet, and a through hole defined by the first implant magnet is in register with a through hole defined by the second implant magnet. The guide catheter defines a lumen and includes a guide magnet affixed to a distal end. The guide magnet defines a through hole in communication with the lumen. The guide magnet is magnetically coupled to one of the first implant magnet and the second implant magnet in an orientation in which the through hole of the guide magnet is in register with the through holes of the first implant magnet and the second implant magnet. An elongate capture member is slid through the lumen until one of a proximal segment and a distal segment extends through the through holes of the guide magnet, the first implant magnet and the second implant magnet. The elongate capture member includes an abutment segment that separates the proximal segment from the distal segment. The abutment segment, the guide magnet, the first implant magnet and the second implant magnet are moved as a group from the implantation site while the abutment segment contacts one of the guide magnet, the first implant magnet and the second implant magnet.

BRIEF DESCRIPTION OF THE DRAWINGS

FIG. 7 shows an elongate capture member according to another aspect of the present disclosure being slid in the lumen of the guide catheter toward the implantation site;

FIG. 8 is a schematic view that shows the elongate capture member of FIG. 7 with its abutment segment enlarged to contact the implanted magnets;

FIG. 9 is a schematic view showing the magnetic retrieval system moving as a group away from the implantation site according to another aspect of this disclosure;

DETAILED DESCRIPTION

Figure 1:
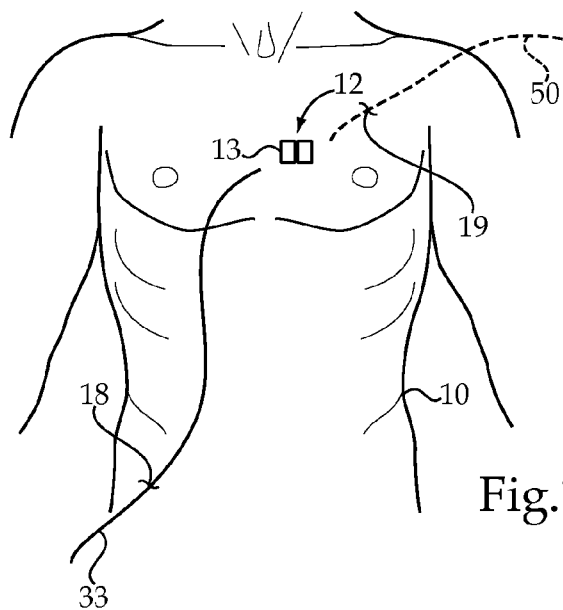
FIG. 1 is a partial schematic view of a pair of implanted magnets positioned at an implantation site in a patients body.

Referring initially to FIG. 1, a pair of previously implanted magnets 13 are located at an implantation site 12 in a patient's body 10. The implanted magnets 13 may have been placed the patient's body 10 to create an anastomosis between two cardiovascular passageways, or the volumes. After the implanted magnets 13 have been in the patient's body 10 for a prescribed period of time, such as several weeks, there may be a desire or need to remove the implanted magnets 13 from the patient's body 10. This disclosure teaches a method and apparatus for retrieving the implanted magnets 13. Depending upon which strategy is utilized, the implanted magnets 13 may be retrieved via a single entry into the patient, such as that first entry site 18, or may utilize two entry sites, such as second entry site 19, in order to retrieve the implanted magnets 13. In most instances, each of the implanted magnets 13 would likely have been originally positioned in the patient's body 10 via two separate entry sites which may have been in close proximity to first and second entry sites 18 and 19, or could have been located elsewhere without departing from the scope of the present disclosure.

Figure 2:
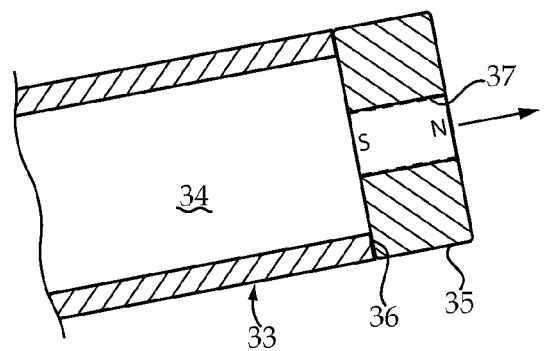
FIG. 2 is a schematic view of a guide catheter being maneuvered toward the fear of implanted magnets of FIG. 1.
Figure 2:
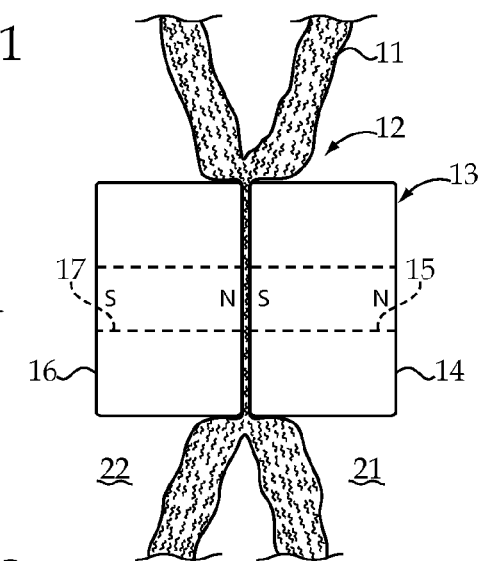
Figure 3:
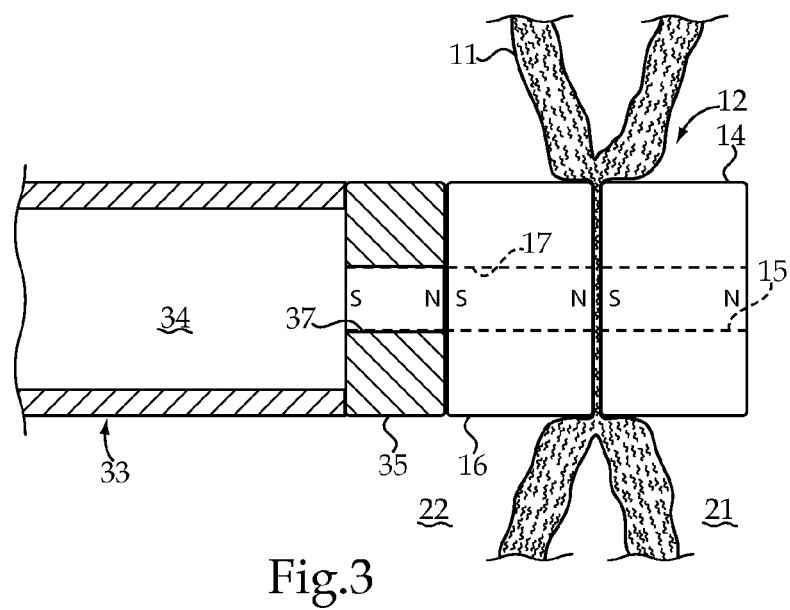
FIG. 3 is a schematic view of a guide catheter of FIG. 2 magnetically coupled to the pair of implanted magnets at the implantation site.

Referring now in addition to FIGS. 2 and 3, the previously implanted magnets 13 include a first implant magnet 14 magnetically coupled to a second implant magnet 16. A through hole 15 defined by the first implant magnet 14 is in register with a through hole 17 defined by the second implant magnet. The first implant magnet 14 may be located in a first volume 21, which may be a first cardiovascular passageway, and the second implant magnet 16 may be located in a second volume, which may be a second and different cardiovascular passageway. Tissue 11 that defines portions of the first and second volumes 21, 22 is squeezed between first implant magnet 14 and second implant magnet 16. A method of retrieving the previously implanted magnets 13 includes maneuvering a guide catheter 33 toward the implantation site 12 utilizing techniques well known in the art via first entry site 18. Guide catheter 33 defines a lumen 34 and includes a guide magnet 35 affixed to a distal end 36. The guide magnet 35 defines a through hole 37 in communication with lumen 34. The magnetic poles (S, N) of the first implant magnet 14 and the second implant magnet 16 are arranged such that the implanted magnets 13 naturally magnetically couple in the configuration shown so that through holes 15 and 17 are in register. Likewise, the north and south poles of the guide magnet 35 are configured such that the guide magnet 35 tends to be attracted to second guide magnet 16 to magnetically couple in the configuration shown in FIG. 3, rather than being attracted toward magnetic coupling along different surfaces. The guide catheter 33 is maneuvered until the guide magnet 35 magnetically couples to one of the first implant magnet 14 and the second implant magnet 16 in an orientation in which the through hole 37 of the guide magnet is in register with the through holes 15, 17 of the first implant magnet 14 and the second implant magnet 16. In the illustrated embodiment, guide magnet 35 is shown magnetically coupled with second implant magnet 16. The portion of the procedure shown in FIGS. 2 and 3 is common to the various different methods and devices illustrated in the following Figures for retrieving the previously implanted magnets 13.

Figure 4:
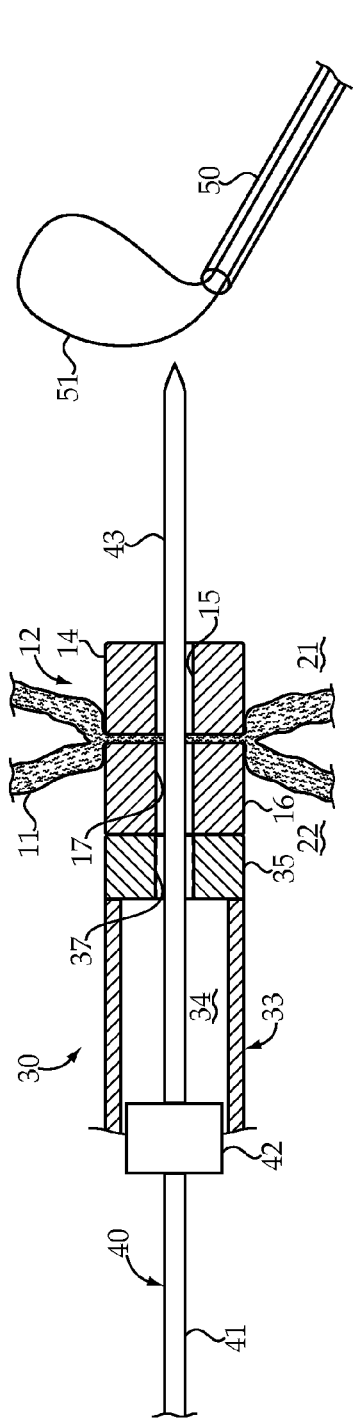
FIG. 4 is a schematic view showing an elongate capture member being slid through the lumen of the guide catheter of FIG. 3 from one direction while a grasping element of a pull approaches the implantation site from an opposite direction.
Figure 5:
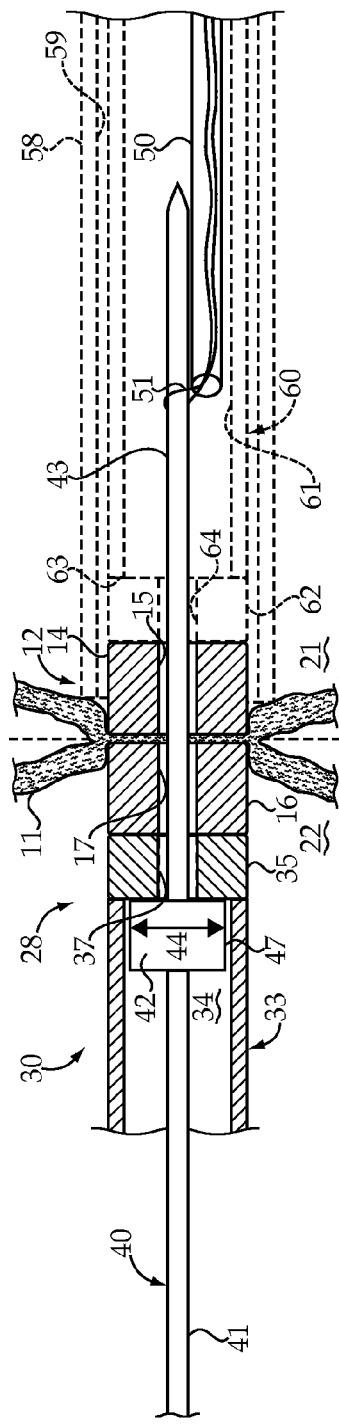
FIG. 5 is a schematic view showing the grasping element coupled to a distal segment of the elongate capture member of FIG. 4.
Figure 6:
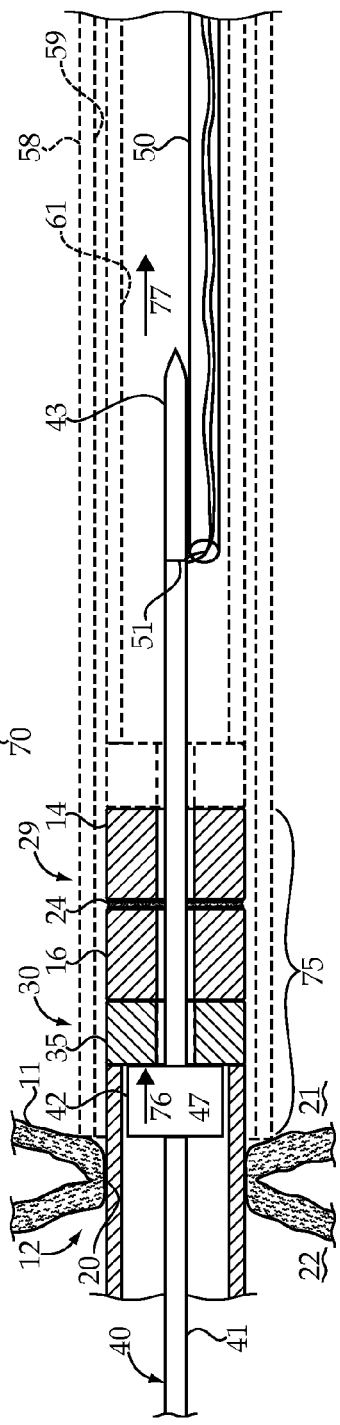
FIG. 6 is a schematic view of the magnetic retrieval system being moved as a group by a pull from the implementation site.

Referring now in addition to FIGS. 4-6, after guide catheter 33 has been properly positioned with guide magnet 35 magnetically coupled to second implant magnet 16 as shown in FIG. 3, an elongate capture member 40 may be slid through lumen 34 until one of a proximal segment 41 and a distal segment 43 extends through the through holes 37, 17, 15 of the guide magnet 35, second implant magnet 16 and first implant magnet 14, respectively. The elongate capture member 40 includes an abutment segment 42 that separates the proximal segment 41 from the distal segment 43. In this embodiment, abutment segment 42 may have a cross section 44 that is larger than the through hole 37 of guide magnet 35. Cross section 44 may be a fixed cross section. In other embodiments, the abutment segment 42 may have an expandable cross section that has a low profile configuration that allows abutment segment 42 to pass through the through holes of the guide and implanted magnets 35, 13. Depending upon the state of the tissue 11 trapped between the first implant magnet 14 and the second implant magnet 16, the distal tip of the elongate capture member 40 may need to be sufficiently sharp to puncture through the necrosis. In this version, the abutment segment has a fixed shape 47 and the cross section 44 is smaller than lumen 34, but larger than the though hole 37 of guide magnet 35. In the strategy illustrated in FIGS. 4-6, a pull 50, which includes a grasping element 51 may approach implantation site 12 via passageway 21 and second entry site 19.

FIG. 5 shows a complete magnet retrieval system 30 in a retrieval configuration 29 in which guide magnet 35 is magnetically coupled to one of the first implant magnet 14 and second implant magnet 16, and one of the proximal segment 41 and distal segment 43 of the elongate capture member 40 extends through the through holes 37, 17, 15 of the guide magnet 35, second implant magnet 16 and first implant magnet 14, respectively. Finally, the retrieval configuration 29 includes the abutment segment 42 in contact with one of the guide magnet 35, the first implant magnet 14 and the second implant magnet 16. In this embodiment, the abutment segment 42 is in contact with the guide magnet 35 as shown in FIG. 5. After achieving the retrieval configuration 29, the abutment segment 42, the guide magnet 35, the first implant magnet 14 and the second implant magnet 16 are moved as a group 75 from the implantation site 12 under the action of pull 50 pulling elongate capture member 40 toward the second entry site 19 through which pull 50 gained access to the patient's body 10. Moving the group 75, which includes abutment segment 42, guide magnet 35, second implant magnet 17 and first implant magnet 15, is accomplished by moving the pull 50 away from the implantation site 12. In the illustration, grasping element 51 is shown as a snare, but those skilled in the art will appreciate that numerous other structures could be substituted, including but not limited to a grasping element in the form of forceps, or possibly even a strategy in which distal segment 43 is received in a wire mesh that is pinched together as a grasping element to capture distal segment 43 of elongate capture member 40. Those skilled in the art will appreciate that guide catheter 33 follows with guide magnet 35 as pull 50 pulls the entire assembly out of the patient's body 10 through second entry site 19 leaving a passage 20 between the first volume 21 and the second volume 22 of the patient's cardiovascular system. When this occurs, a tissue fragment 24, which was squeezed between first implant magnet 14 and second implant magnet 16 may detach and be carried away with group 75. After the proximal segment 41 of elongate capture member 40 and the entire guide catheter 33 exit the patient's body 10, the procedure according to one aspect is completed.

Those skilled in the art will appreciate that the edges of tissue 11 adjacent the pair of implant magnets 13 may grow together over time while the implanted magnets were positioned in the patient's body so that the tissue 11 itself defines passage 20 possibly without the need for any artificial support or other permanent device. Also shown in FIGS. 5 and 6 on the right hand side are an optional second guide catheter 60 and/or an optional outer catheter 58 that may be utilized in the procedure in a manner described infra.

Referring now to FIGS. 7-9, an alternative retrieval process utilizes an elongate capture member 140 with an abutment segment 142 that has an expandable cross section 144. Like the earlier embodiment, elongate capture member 140 includes a proximal segment 141 separated from a distal segment 143 by abutment segment 42. The expandable cross section 144 has a first configuration 145 in which the expandable cross section 144 is smaller than the through holes 37, 17, 15 of guide magnet 35, second implant magnet 17 and first implant magnet 14, respectively. The expandable cross section 144 may be changed to a second configuration 146 as shown in FIG. 8 in which the expandable cross section 144 is larger than the through holes 37, 17, 15 of the guide magnet 35, the second implant magnet 16 and the first implant magnet 14. Those skilled in the art will appreciate that FIGS. 7-9 were preceded by the steps shown in FIGS. 2 and 3. Although not necessary, the elongate capture member 140 may take the form of a malecot that may utilize an actuator pin 148 to change expandable cross section 144 between the first configuration 145 and the second configuration 146. Those skilled in the art will appreciate that a wide variety of devices are known that could be utilized as an elongate capture member 140 with an abutment segment 142 that has an expandable cross section 144 that differ in structure and shape from the malecot type device shown, and those alternative devices would also fall within the intended scope of the present disclosure. The distal segment 141 is moved through the through holes 37, 17, 15 of the guide magnet 35, second implant magnet 16 and first implant magnet 14, respectively. After the distal segment has passed through the through holes 37, 17, 15, the abutment segment 142 is passed through the through holes 37, 17 and 15 while the expandable cross section 144 is in the first configuration 145. The expandable cross section 144 is then changed from the first configuration 145 to the second configuration 146. Thereafter the abutment segment 142 is moved into contact with the first implant magnet 14. The important aspect in this regard is that the expandable cross section can be maneuvered through the through holes 37, 17, 15 in the small diameter first configuration 145, but cannot be maneuvered through the through holes 37, 17, 15 in the large diameter second configuration 146 so that the group 75 can be moved together as shown in FIG. 9 in the reverse direction with the elongate capture member 140. The group includes the abutment segment 142, the guide magnet 35, the second implant magnet 16 and the first implant magnet 14 in a reverse direction and out of the patient's body 10 through the first entry site 18. Thus, the procedure and device illustrated in FIGS. 7-9 allows the previously implanted magnets 13 to be removed from the patient's body 10 utilizing only a single entry site 18. Like the previous strategy, the removal of the magnetic magnet retrieval system 130 leaves a passage 20 between the first volume 21 and the second volume 22.

Figure 10:
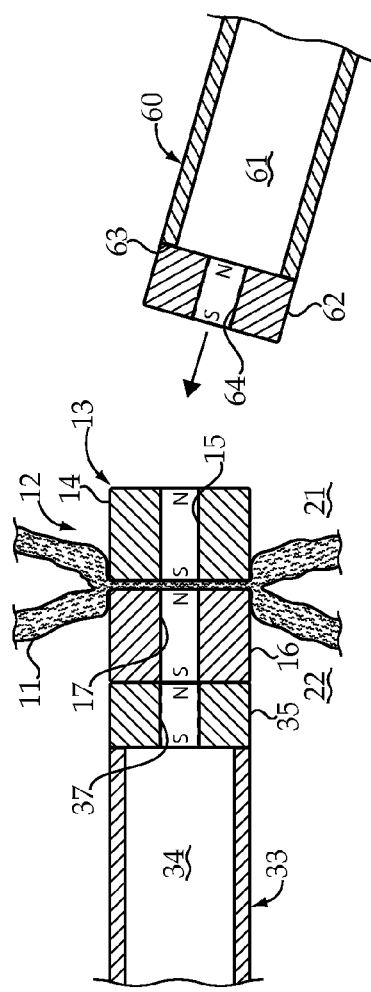
FIG. 10 is a schematic view of an implantation site with a second guide catheter approaching from an opposite side of the implanted magnets.
Figure 11:
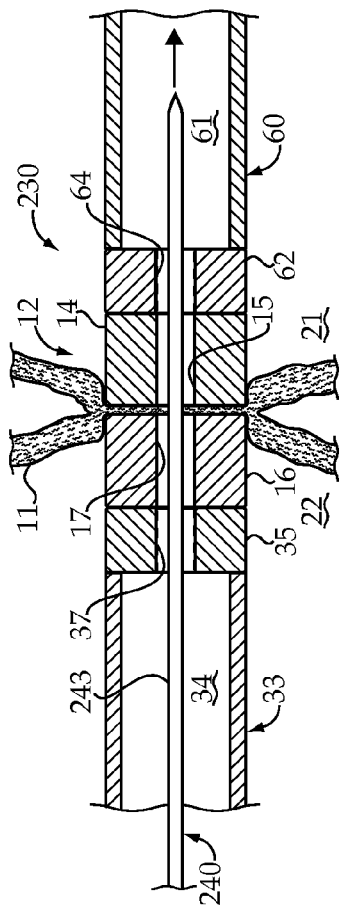
FIG. 11 is a schematic view showing an elongate capture member being slid through the lumens of the first and second guide catheters.
Figure 12:
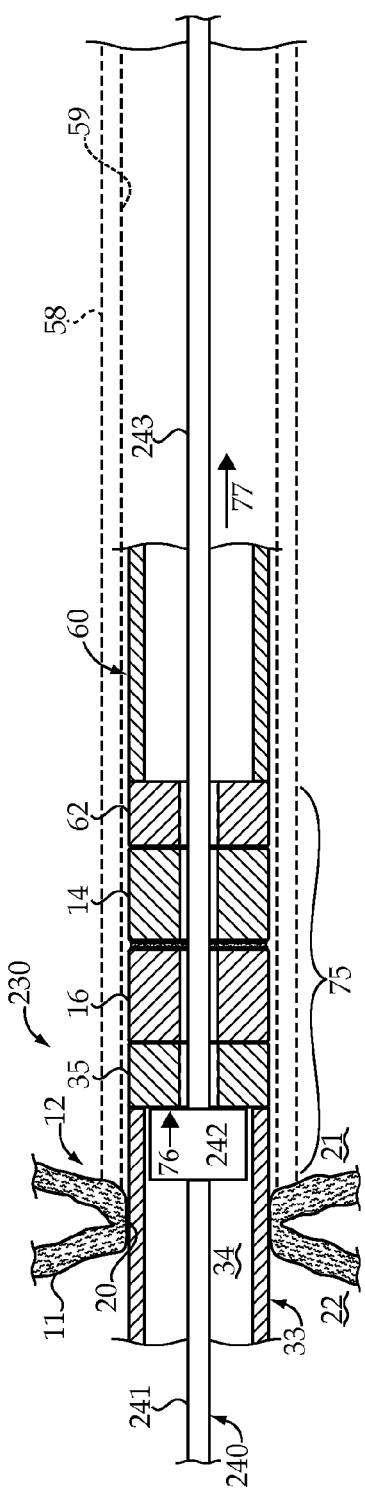
FIG. 12 is a schematic view showing the magnetic retrieval system being moved as a group away from the implantation site according to another aspect of the present disclosure.

Referring now to FIGS. 10, 11 and 12, still another strategy for retrieving a pair of implanted magnets 13 from an implantation site 12 is shown. The steps shown in FIGS. 10-12 are immediately preceded by the previously described steps of FIGS. 2 and 3. After the guide magnet 35 of the first guide catheter is magnetically coupled to the second implant magnet 16, a second guide catheter 60 is maneuvered toward implantation site 12 via second entry site 19 (FIG. 1). Like the first guide catheter 33, second guide catheter 60 defines a lumen 61 and includes a second guide magnet 62 affixed to a distal end 63. The second guide magnet 62 defines a through hole 64 in register with the lumen 61. The second guide magnet 62 is magnetically coupled with one of the first implant magnet 14 and second implant magnet 16 as shown in FIG. 11 in an orientation in which the through hole 64 of the second guide magnet 62 is in register with the through holes 15, 17 of the first implant magnet 14 and the second implant magnet 16. Thereafter, an elongate capture member 240 is moved through lumen 34 so that distal segment 243 moves through the through holes 37, 17, 15, 64 and into lumen 61. This strategy is similar to the strategy shown with relation to FIGS. 4-6, except that the distal segment 243 of the elongate capture member 240 is sufficiently long that a distal portion of distal segment 243 exits the patient's body 10 through second entry site 19 before abutment segment 242 comes into contact with guide magnet 35. This allows for the potential elimination of a separate pull 50 as shown in the earlier embodiment. Instead, the user may simply grasp the distal segment 243 (now functioning as a pull) of the elongate capture member 240 and pull the entire magnet retrieval system 230, which includes the group 75 out of the patient's body through second entry site 19. The second guide catheter 60 ensures that no steering is needed when advancing the distal segment 243 of elongate capture member 240 from first access site 18 through the implanted magnets 13 and out of the second access site 19. Like the earlier embodiments, elongate capture member 240 includes a proximal segment 241 separated from a distal segment 243 by an abutment segment 242, which is illustrated in this embodiment as being a fixed cross section that is larger than the through holes 37, 64 of the guide magnets 35, 62 and the through holes 17, 15 of the implanted magnets 13.

In the event that there is some concern that the implanted magnets 13 will have difficulty detaching from the tissue 11, an optional outer catheter 58 may be utilized. In particular, in the embodiment shown in FIGS. 10-12, an optional outer catheter 58 is shown in FIG. 12. The outer catheter 58 may be slid along the outer surface of second guide catheter 60 after it has become magnetically coupled to the implanted magnets 13. Detaching the first implant magnet 14 and the second implant magnet 16 from tissue 11 at implantation site 12 may be assisted by positioning outer catheter 58 in contact with tissue 11 in opposition to a force 76 of the abutment segment 242 onto the guide magnet 35. As shown, outer catheter 58 defines a lumen 59 sized to receive both first guide catheter 33 and second guide catheter 60, as well as the first and second implant magnets 14, 16. In this optional variation, the entire magnet retrieval system 230 is slid out of the patient's body 10 along lumen 59 of outer catheter 58 and eventually out of second access site 19. This is accomplished, the outer catheter 58 may also be withdrawn out of the patients body 10 through second access site 19 to complete the procedure.

Returning briefly to FIG. 9, an optional outer catheter 58 is shown in dashed lines in order to contact and hold tissue 11 in place when the magnetic retrieval assembly 130 is detached from tissue 11. In this example, the magnetic retrieval system 130 is slid through lumen 59 and out of the patient's body 10 through first access site 18.

Referring back to again to FIGS. 5 and 6, dotted lines show an optional use of a second guide catheter 60 and/or an outer catheter 58. By using a second guide catheter 60, the coupling of the grasping device 51 of pull 50 may be more easily accomplished. The outer catheter 58 may be useful in holding tissue 11 in place while the first implant magnet 14 and the second implant magnet 16 are detached from implantation site 12 responsive to movement of pull 50 and elongate capture member 40.

Referring briefly again to FIG. 5, magnet retrieval system 30 may have a pre-retrieval configuration 28 in which the outer catheter 58 and the abutment segment 42 are located on opposite sides 70 of a plane 71 separating the first implant magnet 14 and the second implant magnet 16. As stated earlier, the outer catheter 58 is sized to receive the first guide catheter 33, the second guide catheter 60, if used, the first implant magnet 14 and the second implant magnet 16. In the embodiments shown in FIGS. 4-6 and 10-12, the elongate capture member 40, 240 is moved in a same direction 77 during both the sliding steps illustrated in FIGS. 4 and 11 as the step in which the abutment segment 42, 242 is moved away from implantation site 12. This is to be contrasted with the embodiment shown in FIGS. 7-9 in which the elongate capture member 140 is moved in opposite directions during sliding and abutment moving steps.

INDUSTRIAL APPLICABILITY

The present disclosure finds general applicability to strategies for retrieving previously implanted magnets in a patient's body. The present disclosure finds specific applicability to retrieving previously implanted magnets 13 from the cardiovascular system of a patient, but may also have applicability in retrieving magnets from other passageways or volumes within a patient's body 10. Finally, the present disclosure finds specific applicability to retrieving implanted magnets 13 in which the first implanted magnet 14 and the second implanted magnet 16 include through holes 15, 17 that are in register at the implantation site 12.

Although the present disclosure has been illustrated, in one aspect, as using a grasping element 51 in the form of a snare with pull 50, those skilled in the art will appreciate that a wide variety of other instruments are known in the art for grasping and holding a distal segment of a catheter-like member as shown, and all of those various devices are considered to fall within the scope of the present disclosure. In addition, another version of the strategy described teaches an elongate capture member 140 with an expandable cross section 144 illustrated in the form of a malecot that is actuated with an actuator pin 148. Nevertheless, those skilled in the art will appreciate that other devices are well known in the art that have the ability to enlarge a segment of cross section between a diameter that could pass through the through holes 15, 17 of the implanted magnets 13 and then be enlarged and be unable to pass back through the same through holes 15, 17 so that the elongate capture member can function as a pull to retrieve the implanted magnets 13 as best shown in FIGS. 7-9. Any of the wide variety of devices that have an expandable cross section capability would also fall within the scope of the present disclosure.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A magnet retrieval system comprising:
    a guide catheter that defines a lumen and includes a guide magnet affixed to a distal end, and the guide magnet defining a through hole in communication with the lumen;
    an elongate capture member slidably received in the lumen and including an abutment segment separating a proximal segment from a distal segment;
    a first implant magnet magnetically coupled to a second implant magnet, and a through hole defined by the first implant magnet being in register with a through hole defined by the second implant magnet;
    wherein the system has a retrieval configuration in which the guide magnet is magnetically coupled to one of the first implant magnet and the second implant magnet, and one of the proximal segment and the distal segment extends through the through holes of the guide magnet, the first implant magnet and the second implant magnet, and the abutment segment is in contact with one of the guide magnet, the first implant magnet and the second implant magnet.

2. The magnetic retrieval system of claim 1 wherein the distal segment extends through the through holes of the guide magnet, the first implant magnet and the second implant magnet;
    a pull with a grasping element coupled to the distal segment of the elongate capture member.

3. The magnet retrieval system of claim 1 wherein the abutment segment has either a cross section that is larger than the through hole of the guide magnet or an expandable cross section;
    the expandable cross section has a first configuration in which the expandable cross section is smaller than the through holes of the guide magnet, the first implant magnet and the second implant magnet, and a second configuration in which the expandable cross section is larger than the through holes of the guide magnet, the first implant magnet and the second implant magnet.

4. The magnet retrieval system of claim 3 wherein the abutment segment includes the expandable cross section.

5. The magnet retrieval system of claim 3 wherein the abutment segment has a fixed shape, and the cross section is smaller than the lumen, and larger than the through hole of the guide magnet.

6. The magnet retrieval system of claim 1 including an outer catheter sized to receive the guide catheter, the first implant magnet and the second implant magnet; and
    the system has a pre-retrieval configuration in which the outer catheter and the abutment segment are located on opposite sides of a plane separating the first implant magnet and the second implant magnet.

7. The magnet retrieval system of claim 6 wherein the abutment segment has either a cross section that is larger than the through hole of the guide magnet or an expandable cross section;
    the expandable cross section has a first configuration in which the expandable cross section is smaller than the through holes of the guide magnet, the first implant magnet and the second implant magnet, and a second configuration in which the expandable cross section is larger than the through holes of the guide magnet, the first implant magnet and the second implant magnet.

8. The magnet retrieval system of claim 7 wherein the abutment segment includes the expandable cross section.

9. The magnet retrieval system of claim 7 wherein the abutment segment has a fixed shape, and the cross section is smaller than the lumen, and larger than the through hole of the guide magnet.

10. The magnet retrieval system of claim 1 wherein the guide catheter is a first guide catheter, and the guide magnet is a first guide magnet;
    a second guide catheter that defines a lumen and includes a distal end;
    a second guide magnet of the second guide catheter being affixed to the distal end, and defining a through hole in communication with the lumen of the second guide catheter;

wherein the retrieval configuration includes the second guide magnet magnetically coupled to an other one of the first implant magnet and the second implant magnet, and one of the proximal segment and the distal segment extends through the through hole of the second guide magnet.

11. The magnet retrieval system of claim 10 including an outer catheter sized to receive the first guide catheter, the second guide catheter, the first implant magnet and the second implant magnet; and the system has a pre-retrieval configuration in which the outer catheter and the abutment segment are located on opposite sides of a plane separating the first implant magnet and the second implant magnet.

12. A method of retrieving previously implanted magnets from an implantation site, the method comprising the steps of:

providing a magnet retrieval system including a guide catheter that defines a lumen and includes a guide magnet affixed to a distal end, and the guide magnet defining a through hole in communication with the lumen; an elongate capture member slidably received in the lumen and including an abutment segment separating a proximal segment from a distal segment; a first implant magnet magnetically coupled to a second implant magnet, and a through hole defined by the first implant magnet being in register with a through hole defined by the second implant magnet; wherein the system has a retrieval configuration in which the guide magnet is magnetically coupled to one of the first implant magnet and the second implant magnet, and one of the proximal segment and the distal segment extends through the through holes of the guide magnet, the first implant magnet and the second implant magnet, and the abutment segment is in contact with one of the guide magnet, the first implant magnet and the second implant magnet;

maneuvering the guide catheter toward the implantation site;

magnetically coupling the guide magnet to one of the first implant magnet and the second implant magnet in an orientation in which the through hole of the guide magnet is in register with the through holes of the first implant magnet and the second implant magnet;

sliding the elongate capture member through the lumen until one of the proximal segment and the distal segment extends through the through holes of the guide magnet, the first implant magnet and the second implant magnet; and moving the abutment segment, the guide magnet, the first implant magnet and the second implant magnet as a group from the implantation site while the abutment segment contacts one of the guide magnet, the first implant magnet and the second implant magnet.

13. The method of claim 12 wherein the distal segment of the elongate capture member extends through the through holes of the guide magnet, the first implant magnet and the second implant magnet;

coupling a grasping element of a pull to the distal segment of the elongate capture member; and the step of moving the abutment segment includes moving the pull away from the implantation site.

14. The method of claim 12 wherein the moving step includes detaching the first implant magnet and the second implant magnet from tissue at the implantation site by positioning an outer catheter in contact with the tissue in opposition to a force of the abutment segment onto the one of the guide magnet, the first implant magnet and the second implant magnet.

15. The method of claim 12 wherein the abutment segment includes an expandable cross section that has a first configuration in which the expandable cross section is smaller than the through holes of the guide magnet, the first implant magnet and the second implant magnet, and a second configuration in which the expandable cross section is larger than the through holes of the guide magnet, the first implant magnet and the second implant magnet;

the sliding step includes moving the proximal segment through the through holes of the guide magnet, the first implant magnet and the second implant magnet, then sliding the abutment segment through the through holes of the guide magnet, the first implant magnet and the second implant magnet while the expandable cross section is in the first configuration;

changing the expandable cross section from the first configuration to the second configuration; and moving the abutment segment into contact with one of the first implant magnet, the second implant magnet and the guide magnet.

16. The method of claim 12 wherein the guide catheter is a first guide catheter, and the guide magnet is a first guide magnet;

maneuvering a second guide catheter toward the implantation site, and the second guide catheter defines a lumen and includes a second guide magnet affixed to a distal end, and the second guide magnet defining a through hole in register with the lumen of the second guide catheter;

magnetically coupling the second guide magnet to the other one of the first implant magnet or the second implant magnet in an orientation in which the through hole of the second guide magnet is in register with the through holes of the first implant magnet and the second implant magnet; and the step of moving the abutment segment includes moving the abutment segment, the first guide magnet, the first implant magnet, the second implant magnet and the second guide magnet as a group away from the implantation site.

17. The method of claim 12 wherein the moving step includes detaching the first implant magnet and the second implant magnet from tissue at the implantation site by positioning an outer catheter in contact with the tissue in opposition to a force of the abutment segment onto the one of the guide magnet, the first implant magnet and the second implant magnet;

wherein the abutment segment includes an expandable cross section that has a first configuration in which the expandable cross section is smaller than the through holes of the guide magnet, the first implant magnet and the second implant magnet, and a second configuration in which the expandable cross section is larger than the through holes of the guide magnet, the first implant magnet and the second implant magnet;

the sliding step includes moving the proximal segment through the through holes of the guide magnet, the first implant magnet and the second implant magnet, then sliding the abutment segment through the through holes of the guide magnet, the first implant magnet and the second implant magnet while the expandable cross section is in the first configuration;

changing the expandable cross section from the first configuration to the second configuration; and moving the abutment segment into contact with one of the first implant magnet, the second implant magnet and the guide magnet.

18. The method of claim 12 wherein the guide catheter is a first guide catheter, and the guide magnet is a first guide magnet;

maneuvering a second guide catheter toward the implantation site, and the second guide catheter defines a lumen and includes a second guide magnet affixed to a distal end, and the second guide magnet defining a through hole in communication with the lumen of the second guide catheter;

magnetically coupling the second guide magnet to the other one of the first implant magnet or the second implant magnet in an orientation in which the through hole of the second guide magnet is in register with the through holes of the first implant magnet and the second implant magnet;

the step of moving the abutment segment includes moving the abutment segment, the first guide magnet, the first implant magnet, the second implant magnet and the second guide magnet as a group away from the implantation;

wherein the distal segment of the elongate capture member extends through the through holes of the first and second guide magnets, the first implant magnet and the second implant magnet;

coupling a grasping element of a pull to the distal segment of the elongate capture member; and the step of moving the abutment segment includes moving the pull away from the implantation site.

19. The method of claim 18 wherein the moving step includes detaching the first implant magnet and the second implant magnet from tissue at the implantation site by positioning an outer catheter in contact with the tissue in opposition to a force of the abutment segment onto the one of the guide magnet, the first implant magnet and the second implant magnet.

20. The method of claim 12 wherein the elongate capture member is moved in a same direction during the sliding step and the step of moving the abutment segment.

* * * * *

UNITED STATES PATENT AND TRADEMARK OFFICE
CERTIFICATE OF CORRECTION

PATENT NO. : 9,943,335 B2
APPLICATION NO. : 14/788920
DATED : April 17, 2018
INVENTOR(S) : Shaun Davis Gittard and Kanishka Ratnayaka Page 1 of 1

It is certified that error appears in the above-identified patent and that said Letters Patent is hereby corrected as shown below:

On the Title Page

The following additional assignee is added:
(73) Assignee: United States of America
as represented by the Department of Health and Human Services
200 Independence Ave., S.W.
Washington D.C., 20201

Signed and Sealed this
Fourteenth Day of April, 2020

Andrei Iancu
*Director of the United States Patent and Trademark Office*